(12) United States Patent
Aarts (10) Patent No.: US 11,207,033 B2
(45) Date of Patent: Dec. 28, 2021

(54) DETERMINATION SYSTEM FOR DETERMINING A HEART FAILURE RISK

(71) Applicant: KONINKLIJKE PHILIPS N.V., Eindhoven (NL)

(72) Inventor: Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 43 days.

(21) Appl. No.: 16/462,996

(22) PCT Filed: Nov. 22, 2017

(86) PCT No.: PCT/EP2017/079985
§ 371 (c)(1),
(2) Date: May 22, 2019

(87) PCT Pub. No.: WO2018/095936
PCT Pub. Date: May 31, 2018

(65) Prior Publication Data
US 2019/0290212 A1    Sep. 26, 2019

(30) Foreign Application Priority Data

Nov. 25, 2016   (EP) .................................. 16200644

(51) Int. Cl.
*A61B 5/05*     (2021.01)
*A61B 5/00*     (2006.01)
(Continued)

(52) U.S. Cl.
CPC .......... *A61B 5/7275* (2013.01); *A61B 5/0205* (2013.01); *A61B 5/053* (2013.01);
(Continued)

(58) Field of Classification Search
CPC ... A61B 5/7275; A61B 5/0205; A61B 5/0456; A61B 5/053; A61B 5/0535;
(Continued)

(56) References Cited

U.S. PATENT DOCUMENTS 8,308,641 B2   11/2012  Moroney, III et al.
8,768,461 B2    7/2014  Stein
(Continued)

FOREIGN PATENT DOCUMENTS

KR    20120116213 A   10/2012
WO      2010067297 A1   6/2010
(Continued)

OTHER PUBLICATIONS

International Search Report and Written Opinion, International Application No. PCT/EP2017/079985, dated Mar. 12, 2018.
(Continued)

*Primary Examiner* — Amanda K Hulbert (57) ABSTRACT

The invention relates to a determination system (1) for determining a heart failure risk for a subject (4). The determination system is adapted to provide a cardiogram selected from a group consisting of a ballistocardiogram, a seismocardiogram and an impedance cardiogram of the subject, to detect at least one of a presence of a postextrasystolic potentiation (PESP) and a disturbed force-frequency relation (FFR) based on the provided cardiogram and to determine the heart failure risk based on this detection. By using the detection of the presence of the PESP and/or of a disturbed FFR, the heart failure risk can be reliably determined. In particular, it can be determined that the heart failure risk is relatively large, if a PESP is not present and/or if the FFR is disturbed.

13 Claims, 5 Drawing Sheets

(51) Int. Cl.
  *A61B 5/0205* (2006.01)
  *A61B 5/053* (2021.01)
  *A61B 5/11* (2006.01)
  *G16H 50/30* (2018.01)
  *A61B 5/0535* (2021.01)
  *A61B 5/352* (2021.01)
  *A61B 5/021* (2006.01)
  *A61B 5/08* (2006.01)

(52) U.S. Cl.
  CPC .......... *A61B 5/0535* (2013.01); *A61B 5/1102* (2013.01); *A61B 5/1107* (2013.01); *A61B 5/1118* (2013.01); *A61B 5/352* (2021.01); *A61B 5/681* (2013.01); *A61B 5/6825* (2013.01); *A61B 5/6829* (2013.01); *A61B 5/6887* (2013.01); *A61B 5/7282* (2013.01); *G16H 50/30* (2018.01); *A61B 5/02125* (2013.01); *A61B 5/0816* (2013.01); *A61B 2562/0252* (2013.01)

(58) Field of Classification Search
  CPC ... A61B 5/1102; A61B 5/1107; A61B 5/1118; A61B 5/681; A61B 5/6825; A61B 5/6829; A61B 5/6887; A61B 5/7282; A61B 5/02125; A61B 5/0816; A61B 2562/0252; A61B 5/352; G16H 50/30
  See application file for complete search history.

(56) References Cited

U.S. PATENT DOCUMENTS

| | | | | |
|---|---|---|---|---|
| 9,585,582 | B2 | 3/2017 | Zong | |
| 9,622,665 | B2 | 4/2017 | Zhang | |
| 2006/0247698 | A1* | 11/2006 | Burnes | A61N 1/3627 607/9 |
| 2007/0179545 | A1* | 8/2007 | Warkentin | A61N 1/36564 607/23 |
| 2009/0209869 | A1* | 8/2009 | Kovacs | G16H 50/30 600/486 |
| 2010/0298901 | A1* | 11/2010 | Sommer | A61N 1/3702 607/14 |
| 2011/0066041 | A1 | 3/2011 | Pandia et al. | |
| 2011/0208016 | A1 | 8/2011 | Bombardini | |
| 2011/0251502 | A1 | 10/2011 | Friedrich et al. | |
| 2012/0065524 | A1 | 3/2012 | Morren et al. | |
| 2014/0288442 | A1* | 9/2014 | Bombardini | A61B 5/0205 600/484 |
| 2015/0065894 | A1 | 3/2015 | Airaksinen et al. | |
| 2015/0164355 | A1* | 6/2015 | Brockway | G06K 9/0053 600/301 |

FOREIGN PATENT DOCUMENTS

| | | |
|---|---|---|
| WO | 2011028016 A2 | 3/2011 |
| WO | 2015036925 A1 | 3/2015 |
| WO | 2015198429 A1 | 12/2015 |
| WO | 2017129426 A1 | 8/2017 |

OTHER PUBLICATIONS

Dinh, A., et al., "Design of a Seismocardiography Using Tri-Axial Accelerometer Embedded with Electrocardiogram", Proceedings of the World Congress on Engineering and Computer Sciences, 2011, vol. II.

Inan, O. et al., "Ballistocardiography and Seismocardiography: A Review of Recent Advances", IEEE Journal of Biomedical and Health Informatics, vol. 19, No. 4, Jul. 2015.

Sinnecker, D. et al., "Postextrasystolic Blood Pressure Potentiation Predicts Poor Outcome of Cardiac Patients", Embase, vol. 3, No. 3, Jun. 2014.

Gupta, A., "Respiration Rate Measurement Based on Impedance Pneumography", Texas Instruments, Feb. 2011.

Gilaberte, S. et al., "Heart and respiratory rate detection on a bathroom scale based on the ballistocardiogram and the continuous wavelet transform", 2010, Annual International Conference of the IEEE Engineering in Medicine and Biology.

Wijshoff, R. et al., "Reduction of Periodic Motion Artifacts in Photoplethysmography", IEEE Transactions on Biomedical Engineering, vol. 64, Issue: 1, Jan. 2017.

Sinnecker, D. et al., "Force-interval relationship predicts mortality in survivors of myocardial infarction with atrial fibrillation", International Journal of Cardiology, 2015.

Cooper, M., "Postextrasystolic Potentiation: Do We Really Know What It Means and How to Use It?", Oct. 2015.

Pieske, B. et al., "Rate Dependence of [Na+] and Contractility in Nonfailing and Failing Human Myocardium", Nov. 2015.

"Heart Failure", Wikipedia, https://en.wikipedia.org/wiki/Heart_failure, Accessed May 2019.

"Myocardial infarction", Wikipedia, https://en.wikipedia.org/wiki/Myocardial_infarction, Accessed May 2019.

"Atrial fibrillation", Wikipedia, https://en.wikipedia.org/wiki/Atrial_fibrillation, Accessed May 2019.

R.A. Cernat, et al., "Real-time extraction of the respiratory rate from photoplethysmographic signal using wearable devices", Workshop on Smart Healthcare and Healing Environments in conjunction with AMI'14, European Conference on Ambient Intelligence http://www.ami-conferences.org/2014 Nov. 11-13, 2014, Eindhoven, The Netherlands.

Health Goods Market, http://www.healthgoods.com/, Accessed May 2019.

* cited by examiner

DETERMINATION SYSTEM FOR DETERMINING A HEART FAILURE RISK

This application is the U.S. National Phase application under 35 U.S.C. § 371 of International Application No. PCT/EP2017/079985, filed on 22 Nov. 2017, which claims the benefit of European Application Serial No. 16200644.9, filed 25 Nov. 2016. These applications are hereby incorporated by reference herein.

FIELD OF THE INVENTION

The invention relates to a determination system, a determination method and a computer program for determining a heart failure risk for a subject.

BACKGROUND OF THE INVENTION

Heart failure (HF), which may also be referred to as a congestive heart failure, chronic heart failure or congestive cardiac failure, describes a situation in which the heart is unable to pump sufficiently to maintain blood flow to meet the needs of a subject's body.

WO 2015/036925 A1 discloses a determination system comprising a sensor for measuring a ballistocardiogram and a signal processing means for determining amplitude variations and frequency variations from the ballistocardiogram and for determining a HF risk based on at least one of these variations. In particular, it is disclosed to quantify the amplitude variation by calculating a standard deviation of peak-to-peak values, wherein the standard deviation is used for determining the HF risk.

WO 2011/0208016 A1 discloses a method and device for the quantification and monitoring of cardiovascular function comprising continuous determination of significant individual cardiovascular function parameters through a multi-sensory, operator-independent platform.

SUMMARY OF THE INVENTION

It is an object of the present invention to provide a determination system, a determination method and a computer program which allow for an improved determination of a HF risk for a subject.

In a first aspect of the present invention a determination system for determining a HF risk for a subject is presented, wherein the determination system comprises:
  a cardiogram providing unit for providing a cardiogram selected from a group consisting of a ballistocardiogram, a seismocardiogram and an impedance cardiogram of the subject, and
  a HF risk determination unit for determining the HF risk based on the cardiogram, wherein the heart failure risk determination unit is adapted to:
  determine peak values for different times, which are indicative of heights of the peaks of the left ventricular pressure over time, based on the provided cardiogram for determining a temporal behavior of characteristics of the left ventricular pressure,
  provide rules which include a first peak value threshold and a second peak value threshold and which define the detection of the presence of a postextrasystolic potentiation (PESP) depending on whether a) a peak value is smaller than the first peak value threshold and b) the following peak value is not larger than the second peak value threshold, and
  determine the heart failure risk based on the determined temporal behavior and the provided rules.

If a PESP is not present, this can indicate a relatively high risk of getting a HF. Thus, by using a detection of a presence of a PESP, the HF risk can be reliably determined and hence an improved HF risk determination can be provided.

The cardiogram providing unit can be a storing unit, in which the cardiogram is stored already, wherein the cardiogram providing unit can be adapted to provide the stored cardiogram. However, the cardiogram providing unit can also be a receiving unit for receiving a cardiogram from a cardiogram measurement unit and for providing the received cardiogram. Moreover, the cardiogram providing unit can be the cardiogram measurement unit itself, wherein the cardiogram providing unit provides the measured cardiogram. A ballistocardiogram, a seismocardiogram and an impedance cardiogram can be provided in an unobtrusive way by using a corresponding sensor without requiring a physician's attendance. The HF risk can therefore be determined in a technically relatively simple way without requiring a physician's attendance.

It should be noted that providing a cardiogram selected from a group consisting of a ballistocardiogram, a seismocardiogram and an impedance cardiogram of the subject means that only a ballistocardiogram, only a seismocardiogram, only an impedance cardiogram or a combination of two or three of these cardiograms can be provided. Generally, it should be noted that the expression "at least one of A and B" and the expression "A and/or B" include the options a) A without B, b) B without A, and c) A and B.

The HF risk determination unit is adapted to determine peak values for different times, which are indicative of the heights of the peaks of the left ventricular pressure over time, for determining the temporal behavior. The HF risk determination unit is adapted to provide rules which include a first peak value threshold and a second peak value threshold and which define the detection of the presence of the postextrasystolic potentiation depending on whether a) a peak value is smaller than the first peak value threshold and b) the following peak value is not larger than the second peak value threshold. By determining whether a peak value is smaller than a first peak value threshold and the following peak is not larger than a second peak value threshold, it can be reliably determined whether a PESP of a healthy heart is present.

In a preferred embodiment the HF risk determination unit is adapted to provide rules defining that the HF risk is larger, if a peak value is smaller than the first peak value threshold and the following peak value is not larger than the second peak value threshold, and smaller, if a peak value is smaller than the first peak value threshold and the following peak value is larger than the second peak value threshold. Thus, preferentially the HF risk, which is determined if the peak value is smaller than the first peak value threshold and the following peak value is not larger than the peak value threshold, is larger than the HF risk, which is determined if the peak value is smaller than the first peak value threshold and the following peak value is larger than the second peak value threshold. In a healthy heart, a peak value, which is smaller than the first peak value threshold, can relate to a so-called "ineffective beat" and the following peak value, which is larger than the second peak value threshold, can relate to a so-called "potentiated beat". This ineffective beat and the following potentiated beat can indicate the PESP of the healthy heart. If an ineffective beat is not followed by a potentiated beat, this can indicate a relatively high risk of getting a HF. This embodiment therefore allows for a further improved determination of the HF risk.

In an embodiment the HF risk determination unit is further adapted to detect a presence of a disturbed force-frequency relation (FFR) based on the provided cardiogram and to determine the heart failure risk based on the detection of the presence of the disturbed force-frequency relation. If the force-frequency relation, i.e. the relation between the frequency of the left ventricular pressure of the heart and the heights of the peaks of the left ventricular pressure, is disturbed, i.e. deviates from the known force-frequency relation to be expected for a healthy heart, this can also indicate a relatively high risk of getting a HF. Thus, by using a detection of a presence of a PESP and a disturbance of the force-frequency relation, the HF risk determination can be further improved.

Preferentially, the heart failure risk determination unit is adapted to a) determine further, for determining the temporal behavior of characteristics of the left ventricular pressure, frequency values for different times, which are indicative of the frequency of the left ventricular pressure over time, based on the provided cardiogram, provide rules defining the heart failure risk depending on the determined temporal behavior, wherein the rules define a detection of the disturbed force-frequency relation based on the determined temporal behavior, and determine the heart failure risk based on the determined temporal behavior and the provided rules. In particular, the HF risk determination unit is adapted to provide rules which define the detection of the disturbed force frequency relation depending on whether the frequency values increase over time, while the peak values do not increase over time. Moreover, in a preferred embodiment the HF risk determination unit is adapted to provide rules defining that the HF risk is larger, if the frequency values increase over time, while the peak values do not increase over time, and smaller, if the frequency values increase over time, while the peak values increase over time. Thus, the HF risk which is determined if the frequency values increase over time, while the peak values do not increase over time, is larger than the HF risk which is determined if the frequency values increase over time, while the peak values increase over time. It is assumed that in a healthy heart having a normal force-frequency relation, the height of the peaks of the left ventricular pressure increases if the frequency of the left ventricular pressure increases. If this healthy behavior of the heart is not observed, the risk of getting a HF can be relatively high and this can be used by the HF risk determination unit for further improving the determination of the HF risk.

The temporal behavior of characteristics of the left ventricular pressure can be similar to the temporal behavior of corresponding characteristics of the provided cardiogram. Thus, for instance, peak values, which are indicative of the heights of the peaks of the left ventricular pressure, and their temporal positions may be determined by determining peak values of the cardiogram, wherein known extraction techniques may be used like the techniques generally used for detecting peaks in an electrocardiogram (ECG).

The determination system can further comprise an activity state providing unit for providing an indication of the activity state of the subject, wherein the HF risk determination unit can be adapted to determine the HF risk also under consideration of the activity state. In particular, the HF risk determination unit is adapted to provide rules which include an activity frequency threshold that depends on the activity state and which define the HF risk also depending on whether the frequency values are larger than the activity frequency threshold for the respective activity state. For instance, the HF risk determination unit can be adapted to determine a larger HF risk, if the frequency values are larger than the activity frequency threshold for the respective activity state, and a smaller HF risk, if the frequency values are smaller than the activity frequency threshold for the respective activity state. Thus, the HF risk which is determined, if the frequency values are larger than the activity frequency threshold for the respective activity state, is larger than the HF risk which is determined, if the frequency values are smaller than the activity frequency threshold for the respective activity state. By also considering the activity state of the subject, for instance, whether the subject is resting, especially sleeping, or walking, the accuracy of determining the HF risk can be further improved. In particular, it can be considered that, if the frequency is relatively high and the subject is resting, this may indicate a relatively high HF risk, whereas, if the frequency is relatively high and the subject is walking or running, the relatively high frequency does not indicate a relatively large risk of getting a HF.

It is further preferred that the HF risk determination unit is adapted to provide rules which include a frequency deviation threshold and which define the HF risk also depending on whether a deviation between temporally consecutive frequency values is larger than a frequency deviation threshold. In particular, the HF risk determination unit can be adapted to provide rules which define that the HF risk is larger, if a deviation between temporally consecutive frequency values is larger than the frequency deviation threshold, and smaller, if a deviation between temporally consecutive frequency values is smaller than the frequency deviation threshold. Thus, the HF risk, which is determined if a deviation between temporarily consecutive frequency values is larger than the frequency deviation threshold, can be larger than the HF risk, which is determined if a deviation between temporarily consecutive frequency values is smaller than the frequency deviation threshold. A frequency value, which may be defined by the inverse of the temporal distance between two consecutive peaks and hence which is indicative of the temporal distance between two consecutive peaks, can indicate the degree of regularity of the heart beat. If the changes between temporally consecutive frequency values are larger than the frequency deviation threshold, this can indicate a relatively large irregularity in the heart beat and hence atrial fibrillation (AF). If AF is detected, the risk of getting a HF can be relatively large, wherein this knowledge can also be used by the HF risk determination unit for determining the HF risk.

In an embodiment the HF risk is binary, i.e. the HF risk determination unit can be adapted to determine either that the HF risk is zero or relatively small or that the HF risk is relatively large. This can be regarded as assigning the subject to one of two degrees of HF risk. The HF risk determination unit can also be adapted to determine to which degree of more than two degrees of HF risk the subject needs to be assigned based on the provided cardiogram.

It is also preferred that the determination system comprises a breathing rate providing unit for providing the breathing rate of the subject, wherein the HF risk determination unit is adapted to determine the HF risk also based on the provided breathing rate. This can lead to a further improved accuracy of determining the HF risk. In a preferred embodiment the HF risk determination unit is adapted to provide a breathing rate threshold that depends on the activity state and to determine the HF risk also depending on whether the breathing rate is larger than the breathing rate threshold for the respective activity state. By also considering the activity state of the subject, for instance, whether the subject is resting, especially sleeping, or walking, the accuracy of determining the HF risk can be further improved. In particular, it can be considered that, if the breathing rate is relatively high and the subject is resting, this may indicate a relatively high HF risk, whereas, if the breathing rate is relatively high and the subject is walking or running, the relatively high breathing rate may not indicate a relatively high risk of HF. The breathing rate providing unit is preferentially adapted to determine the breathing rate based on the cardiogram and to provide the determined breathing rate. This allows determining the breathing rate without requiring an additional device like a chest belt or a flow sensor, thereby allowing for the provision of the breathing rate in a very unobtrusive way.

The above mentioned rules can be combined for determining the HF risk. In particular, the HF risk determination unit can be adapted to determine the HF risk by a) determining whether a peak value is smaller than a first peak value threshold and the following peak is not larger than a second peak value threshold, in order to detect whether a PESP is present, and optionally b) determining the HF risk depending on whether the frequency values increase over time, while the peak values do not increase over time, in order to detect a disturbed force-frequency relation. Moreover, optionally for determining the HF risk also at least one of c) the change of the frequency of the left ventricular pressure depending on the activity state, d) the deviation between temporarily consecutive frequency values and e) the breathing rate can be considered.

In an embodiment the cardiogram providing unit comprises a feet cardiogram measuring unit for measuring the cardiogram via the feet of the subject, while the subject stands on the feet cardiogram measuring unit. In particular, an impedance cardiogram can be measured by using two pairs of electrodes of the feet cardiogram measuring unit, wherein a respective pair of electrodes is arranged for being in contact with the respective foot of the subject if the subject is standing on the feet cardiogram measuring unit. The feet cardiogram measuring unit can also be adapted to measure another kind of cardiogram like a ballistocardiogram by using, for instance, a load cell. This allows measuring the cardiogram in a way which is very unobtrusive for the subject, because the subject just needs to stand on the feet cardiogram measuring unit. This further improves the determination system for determining the HF risk for the subject.

The feet cardiogram measuring unit can be further adapted to measure at least one of the weight and the body composition of the subject. Thus, the subject only needs to stand on the feet cardiogram measuring unit and also the weight and/or the body composition of the subject can be measured, i.e. several different properties of the subject can be measured in a single procedure by just requiring the subject to stand on the feet cardiogram measuring unit, thereby further improving the determination system for determining the HF risk for the subject.

The feet cardiogram measuring unit can comprise a load cell for measuring the weight and the cardiogram. Since the same element, i.e. the load cell, can be used for measuring the weight and also for measuring the cardiogram, it is not necessary to provide two separate elements for measuring the weight and for measuring the cardiogram. This reduces the number of elements of the feet cardiogram measuring unit and hence allows for a simplification of the process of manufacturing the determination system for determining a HF risk for a subject and for a reduction of weight of the determination system, thereby further improving the same.

The cardiogram providing unit can further comprise a handheld cardiogram measuring unit for allowing for a measurement of the cardiogram via the handheld cardiogram measuring unit. This allows measuring the cardiogram, even if the cardiogram cannot be measured via the feet, because, for instance, the subject wears shoes. The handheld cardiogram measuring unit can be adapted to be arranged on the chest of the subject, in order to allow the subject to measure the cardiogram by using the handheld cardiogram measuring unit. It can be adapted to measure an impedance cardiogram or another kind of cardiogram. This further improves the determination system for determining a HF risk for a subject.

It is further preferred that the determination system comprises a sending unit for sending the determined HR risk to an external device. The external device is, for instance, a device with a medical record of the subject, wherein the determined HR risk should be added to the medical record. However, the external device can also be another device like an alarm device for giving an alarm if the determined HR risk indicates that medical measures should be started for reducing the HR risk. The sending unit and the external device are adapted to send the determined HR risk from the sending unit to the external device by using a wireless and/or wired data connection. For instance, the sending unit can be adapted to wirelessly send the determined HR risk to a receiving unit being connected to the external device via a wired data connection.

In a further aspect of the present invention a determination method for determining a HF risk for a subject is presented, wherein the determination method comprises:
providing a cardiogram selected from a group consisting of a ballistocardiogram, a seismocardiogram and an impedance cardiogram of the subject by a cardiogram providing unit,
determining the HF risk based on the cardiogram by a HF risk determination unit,
wherein the HF risk determination unit i) determines peak values for different times, which are indicative of heights of the peaks of the left ventricular pressure over time, based on the provided cardiogram for determining a temporal behavior of characteristics of the left ventricular pressure, ii) provides rules which include a first peak value threshold and a second peak value threshold and which define the detection of the presence of a PESP depending on whether a) a peak value is smaller than the first peak value threshold and b) the following peak value is not larger than the second peak value threshold, and ii) determines the heart failure risk based on the determined temporal behavior and the provided rules.

In another aspect of the present invention a computer program for determining a HF risk for a subject is presented, wherein the computer program comprises program code means for causing a determination system as defined in claim 1 to carry out the determination method as defined in claim 12, when the computer program is run on the determination system.

It shall be understood that the determination system of claim 1, the determination method of claim 12, and the computer program of claim 13 have similar and/or identical preferred embodiments, in particular, as defined in the dependent claims. It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
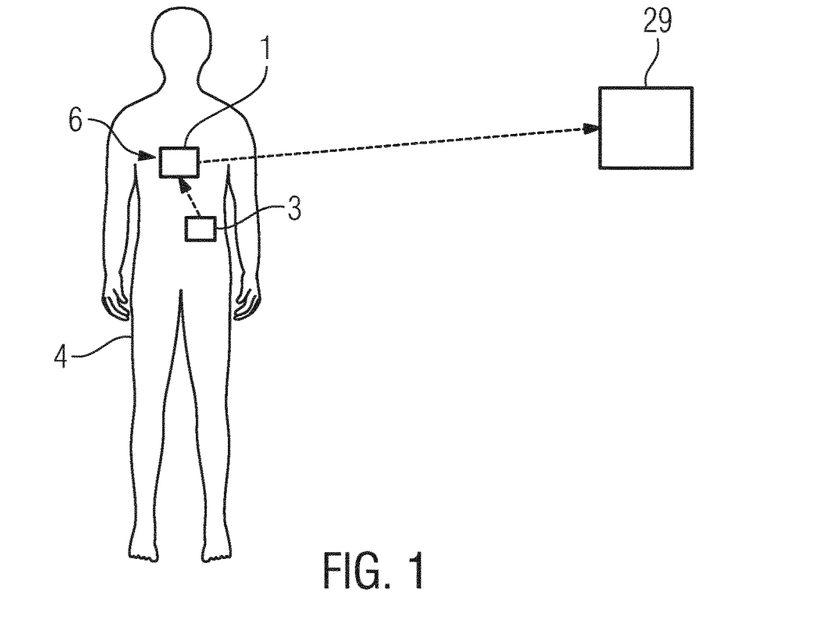
FIG. 1 shows schematically and exemplarily a person with an embodiment of a determination system for determining a HF risk.

FIG. 1 shows schematically and exemplarily a person 4 wearing an embodiment of a determination system 1 for determining a HF risk. The determination system 1 is attached to the chest 6 of the person 4 and schematically and exemplarily shown in more detail in FIG. 2.

Figure 2:
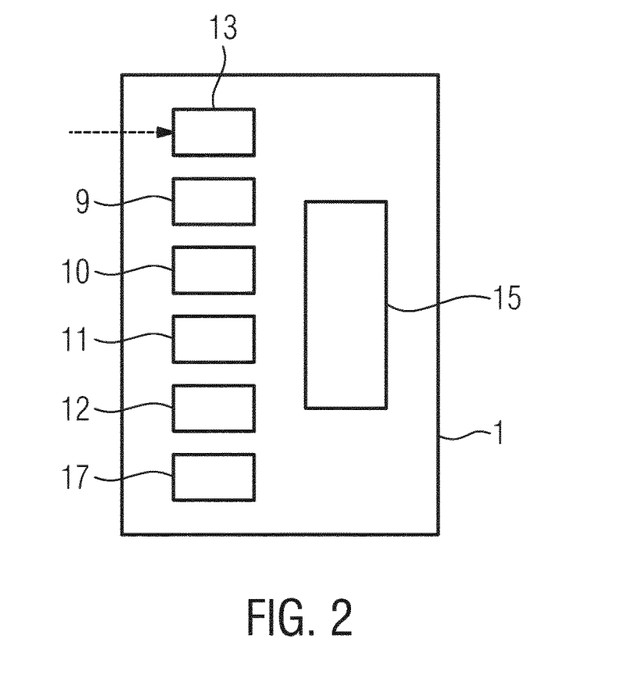
FIG. 2 shows schematically and exemplarily the determination system for determining the HF risk in more detail.

The determination system 1 comprises a cardiogram providing unit 9 for providing a cardiogram selected from a group consisting of a ballistocardiogram, a seismocardiogram and an impedance cardiogram of the person 4. In this embodiment the cardiogram providing unit 9 is adapted to measure a ballistocardiogram. The ballistocardiogram can be measured by using known techniques like measuring the ballistocardiogram with an accelerometer, which might be attached to the chest or to another part of the body like the wrist, for instance, as disclosed in US 2011/0066041 A1 or US 2012/0065524 A1 which are herewith incorporated by reference. It is also possible to measure a ballistocardiogram based on a measurement at the neck by using, for example, a neck collar as disclosed, for instance, in U.S. Pat. No. 8,308,641 B2 which is herewith incorporated by reference.

The determination system 1 further comprises an activity state providing unit 13 for providing an indication of the activity state of the person 4. In this embodiment the activity state providing unit 13 is adapted to receive an accelerometer signal from an accelerometer 3, which is also attached to the person 4, and to determine the acceleration state based on the accelerometer signal received from the accelerometer 3. In FIG. 1, the accelerometer 3 is attached to a hip region of the person 4. In another embodiment the accelerometer 3 can also be attached to another part of the person 4 like, for instance, the wrist of the person 4. The accelerometer could also be integrated in the determination system 1.

The accelerometer signal is indicative of the activity state of the person 4. For instance, the accelerometer signal can indicate whether the person 4 is resting, especially sleeping, or whether the person 4 is walking or running. The activity state providing unit 13 can directly provide the received accelerometer signal as the indication of the activity state or it may process the received accelerometer signal. In particular, the activity state providing unit 13 can comprise rules defining an activity state class among a group of predefined activity state classes like resting, walking, running, et cetera, based on the received accelerometer signal, can determine a current activity class based on the rules and based on a current accelerometer signal, and can provide the determined activity state class as the indication of the activity state of the person 4.

The determination system 1 further comprises a breathing rate providing unit 11 for providing the breathing rate of the person 4 based on the cardiogram provided by the cardiogram providing unit 9. For extracting the breathing rate from the cardiogram known breathing rate extraction techniques can be used like the extraction techniques disclosed in US 2011/0066041 A1, US 2012/0065524 A1 and U.S. Pat. No. 8,308,641 B2. If in another embodiment the cardiogram is an impedance cardiogram, the breathing rate extraction technique disclosed in the Application Report "Respiration Rate Measurement Based on Impedance Pneumography" by Amit K. Gupta, Texas Instruments, SBAA181, February 2011 or another extraction technique might be used.

The determination system 1 further comprises an HF risk determination unit 10 for determining the temporal behavior of characteristics of the left ventricular pressure based on the cardiogram and to provide rules defining the HF risk depending on the determined temporal behavior and optionally further depending on the breathing rate, wherein the HF risk determination unit 10 is further adapted to determine the HF risk based on the provided rules and based on the determined temporal behavior and optionally also the breathing rate. In this embodiment the HF risk determination unit 10 is adapted to determine peak values for different times, which are indicative of the heights of the peaks of the left ventricular pressure over time, and to determine frequency values for different times, which are indicative of the frequency of the left ventricular pressure over time, for determining the temporal behavior. Moreover, the HF risk determination unit 10 is adapted such that the provided rules define a first peak value threshold, a second peak value threshold, an activity frequency threshold, a frequency deviation threshold and a breathing rate threshold.

The HF risk determination unit 10 is adapted to provide the rules such that they define the HF risk depending on at least one of a) whether a peak value is smaller than the first peak value threshold and the following peak value is not larger than the second peak value threshold, in order to detect whether a PESP is present, b) whether the peak values do not increase while the frequency values increase, in order to detect whether the force-frequency relation is disturbed, c) whether a deviation between temporally consecutive frequency values is larger than the frequency deviation threshold, d) whether the frequency values are larger than the activity frequency threshold for the respective activity state, and e) whether the breathing rate is larger than the breathing rate threshold for the respective activity state.

In this embodiment the rules define two degrees of HF risk only, wherein a first degree indicates that the HF risk is zero or relatively small and a second degree indicates a relatively large HF risk. If the HF risk determination results in the second degree, an alarm unit 12 generates an alarm, which might be optical and/or acoustical and/or tactile, in order to indicate that the second degree of HF risk has been determined. The components of the determination system 1 are controlled by a controller 15, and the determination system further comprises a sending unit 17 for sending the determined HF risk to an external device 29 comprising a health record of the person 4 via a wired and/or wired data connection.

The rules can be predefined or they can be learned from a patient during use. For instance, the rules can be determined based on measurements performed at a population of patients, wherein it is known which of these patients have which degree of HF risk. Rules can also be obtained from literature, for instance, from the article "Postextrasystolic Blood Pressure Potentiation Predicts Poor Outcome of Cardiac Patients" by D. Sinnecker et al., Journal of the American Heart Association, 2014, which is herewith incorporated by reference.

The rules can define that the first degree of HF risk is present, if none of the above mentioned conditions used by the HF risk determination unit for determining the HF risk is fulfilled. The HF risk determination unit can further be adapted to determine that the second degree of HF risk is present, if at least one of these conditions is fulfilled. In an embodiment the HF risk determination unit can be adapted to determine a HF risk from a larger group of degrees of HF risk, which comprises more than two degrees, i.e. in an embodiment the HF risk is not binary. For instance, if none of the above mentioned conditions is fulfilled, the HF risk determination unit can determine the smallest degree of HF risk. If all conditions are fulfilled, the HF determination unit can determine the largest degree of HF risk. The rules can further define intermediate degrees of HF risks, which correspond to situations, in which some, but not all, of the conditions are fulfilled.

The cardiogram providing unit 9 is preferentially adapted to provide the cardiogram continuously in realtime. Moreover, also the activity state providing unit 13 is preferentially adapted to provide the indication of the activity state of the person 4 in realtime. This allows the breathing rate providing unit 11 to continuously provide the breathing rate in realtime and the HF risk determination unit 10 to determine the respective degree of HF risk also in realtime. The HF risk can therefore be continuously monitored and, if necessary, an alarm can be generated.

Figure 3:
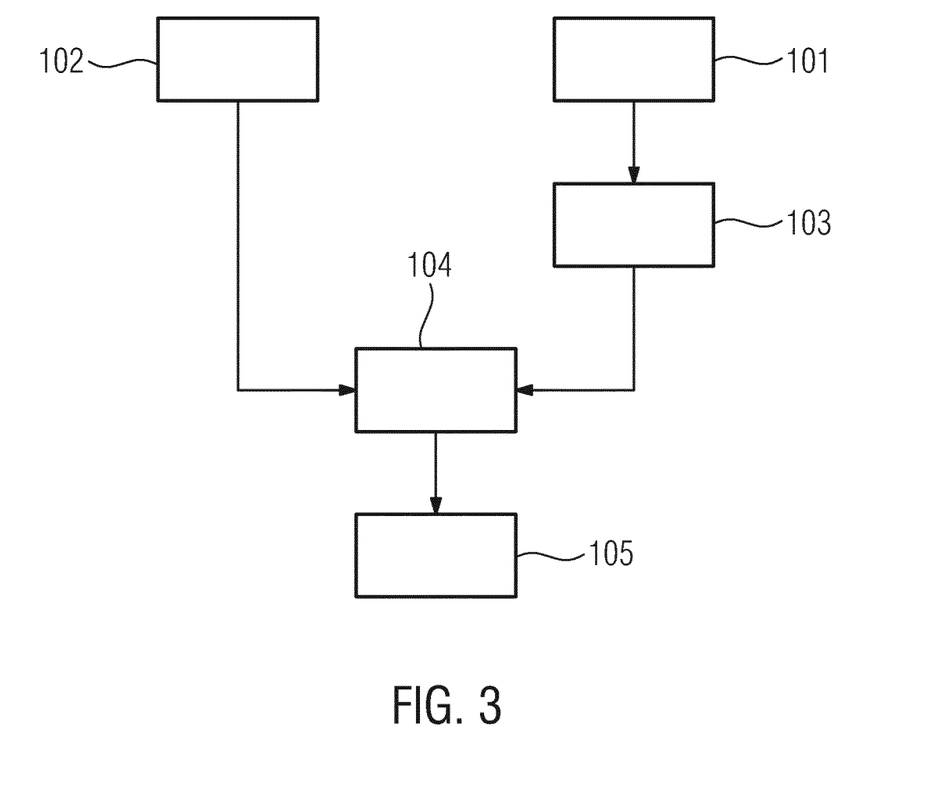
FIG. 3 shows flowchart exemplarily illustrating an embodiment of a determination method for determining a HF risk.

In the following an embodiment of a determination method for determining a HF risk of the person 4 will exemplarily be described with reference to a flowchart shown in FIG. 3.

In step 101 the cardiogram providing unit 9 provides a cardiogram selected from a group consisting of a ballistocardiogram, a seismocardiogram and an impedance cardiogram of the person 4. In step 102 the activity state providing unit 13 provides an indication of the activity state of the person 4, and in step 103 the breathing rate providing unit 10 determines the breathing rate based on the provided cardiogram. In step 104 the HF risk determination unit 10 determines a degree of HF risk based on the provided indication of the activity state of the person 4, the determined breathing rate and the provided cardiogram, wherein the HF risk determination unit 10 determines the temporal behavior of characteristics of the left ventricular pressure based on the cardiogram, provides rules defining the HF risk depending on the determined temporal behavior and the breathing rate, and determines the HF risk based on the provided rules and based on the determined temporal behavior and the breathing rate. In step 105 it is determined whether the degree of HF risk suffices the generation of an alarm or not, wherein in the first case the alarm unit 12 generates an alarm. For instance, if the lowest degree of HF risk, which indicates a HF risk of zero or only a very small HF risk, has been determined in step 104, an alarm may not be generated in step 105, wherein, if a large degree of HF risk has been determined, an alarm may be generated.

A HF occurs when the heart is unable to pump sufficiently to maintain blood flow to meet the body's needs. Signs and symptoms can include shortness of breath, excessive tiredness and leg swelling. The shortness of breath can be worse with exercise, but can also be present while lying down and may even wake the person at night. Causes of HF include coronary artery disease including a previous myocardial infarction, high blood pressure, AF, valvular heart disease, excessive alcohol use, infection, cardiomyopathy of an unknown cause, et cetera. The HF may be caused by changing either the structure or the functioning of the heart. Myocardial infarction, especially acute myocardial infarction, occurs when blood flow stops to a part of the heart causing damage to the heart muscle. AF is an abnormal heart rhythm characterized by rapid and irregular beating. AF can start as brief periods of abnormal beating which become longer and possibly constant over time. PESP includes an increase in contractility that follows an extra systole.

Figure 4:
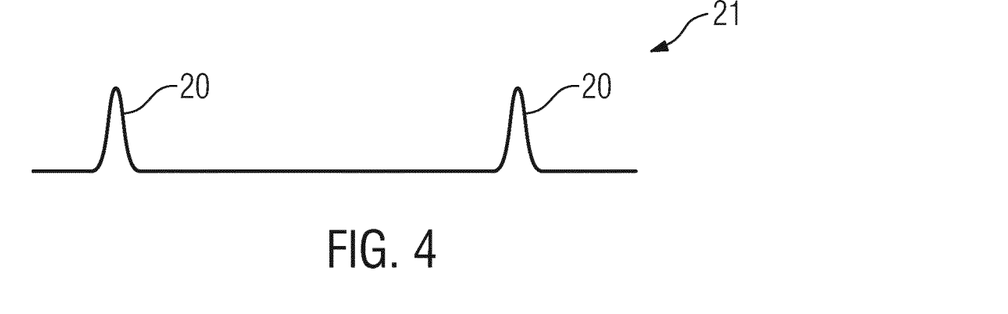
FIG. 4 illustrates exemplarily ventricular pressure over time for a resting person.
Figure 5:
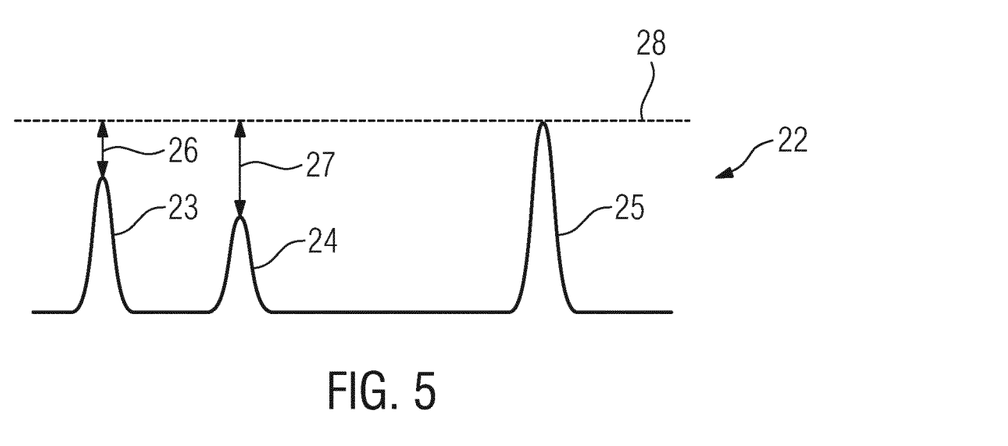
FIG. 5 illustrates exemplarily ventricular pressure over time showing PESP.

PESP is independent of muscle loading and represents a distinct property of the myocardium. FIG. 4 schematically and exemplarily shows the ventricular pressure 21 with peaks 20 without PESP in a rest situation. FIG. 5 shows the ventricular pressure 22 of a person with normal PESP. If PESP is present, after a heart beat 23 an ineffective beat 24 follows, wherein the ineffective beat 24 is followed by a potentiated beat 25. In FIG. 5 the height of the peak 25 is indicated by line 28 and the height differences between the peaks 23, 24 and the peak 25 are indicated by double arrows 26, 27, respectively. In an embodiment the height difference 26 and/or the height difference 27 may be used for determining the HF risk. For instance, the HF risk determination unit can be adapted to provide rules which include a first peak value threshold and a second peak value threshold and which define the HF risk depending on whether a) a peak value of a peak 24 is smaller than the first peak value threshold and b) a peak value of a following peak 25 is not larger than the second peak value threshold. The HF risk determination unit can also be adapted to provide rules which consider peaks only at certain temporal positions defined by a given frequency, i.e. by considering peaks only, which correspond to the given frequency. The frequency is preferentially given by previous waves of the cardiogram. For instance, previous cardiogram waves can correspond to the left ventricular pressure shown in FIG. 6 having a certain frequency. In FIG. 5 peaks 23 and 25 correspond to this frequency such that these peaks 23, 25 may be used for determining the HF risk such that the peak 25 can be regarded as being the peak following the peak 23. In particular, the rules can include a first peak value threshold and a second peak value threshold and define the HF risk depending on whether a) the peak value of the peak 23 is smaller than the first peak value threshold and b) the peak value of the following peak 25 is not larger than the second peak value threshold.

Figure 6:
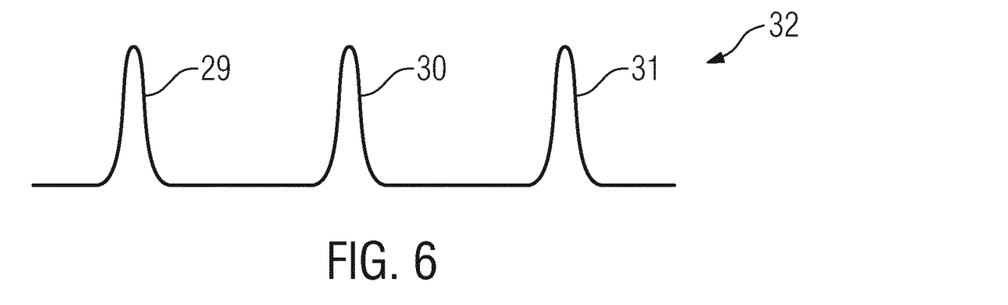
FIG. 6 illustrates exemplarily ventricular pressure over time for a non-resting person.

FIG. 6 shows the ventricular pressure 32 of a person with a normal FFR, i.e. in comparison to FIG. 4 the peak values indicating the heights of the peaks 29, 30, 31 are larger and the frequency is also larger. Hence, the HF risk determination unit can be adapted to provide rules which define the HF risk depending on whether the frequency values increase over time, while the peak values do not increase over time. In particular, the HF risk determination unit can be adapted to provide rules which define that the HF risk is larger, if the frequency values increase over time, while the peak values do not increase over time, and smaller, if the frequency values increase over time, while the peak values increase over time.

The determination system is preferentially adapted to determine the HF risk by detecting a lack of potentiation based on the provided ballistocardiogram, wherein instead of the ballistocardiogram also a seismocardiogram or an impedance cardiogram might be used. The determination system can detect a disturbed force-frequency relation or irregularities of the heartbeat like PESP or another irregularity like AF based on the ballistocardiogram, seismocardiogram or impedance cardiogram. If the determination system is adapted to detect AF, this can be combined with the determination whether PESP is present, in order to further increase the reliability of determining the HF risk. For detecting AF the HF risk determination unit may be adapted to determine whether changes between temporally consecutive frequency values are larger than a frequency deviation threshold.

The determination system can be a single device, which can detect a PESP and/or a disturbed force-frequency relation, in order to determine the HF risk. However, the determination system can also be comprised of several separated components which communicate to each other.

Although in above described embodiments the determination system is attached to the chest of the person, in other embodiments the determination system can be adapted to be attached to another part of the person. For instance, the determination system can be a watch-like device to be worn at the wrist of the person. The determination system can also be an in-ear device. The determination system can also be adapted to measure the cardiogram via the feet and to use this cardiogram for determining the HF risk as will be explained in the following.

Figure 7:
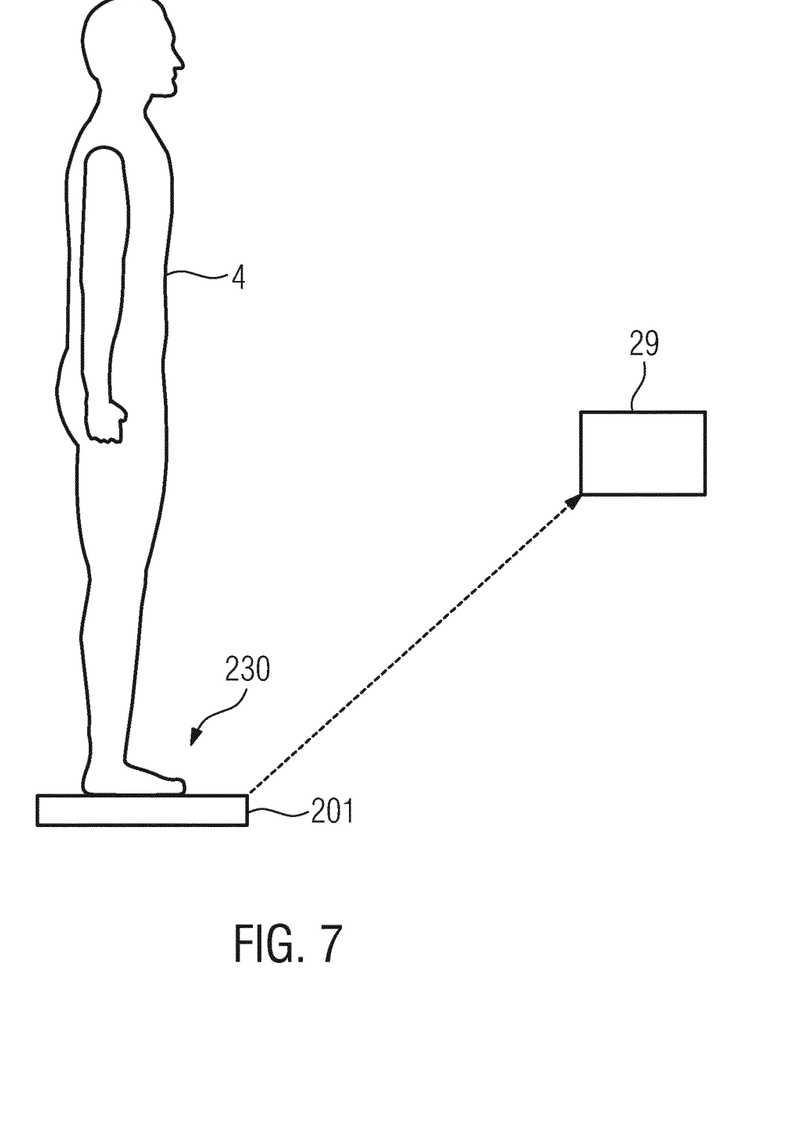
FIG. 7 shows schematically and exemplarily a person with a further embodiment of a determination system for determining a HF risk.

FIG. 7 schematically and exemplarily shows an embodiment of a determination system 201 for determining a HF risk for a subject, which is adapted to allow a person 4 to stand on the determination system 201 for measuring an impedance cardiogram via the feet 230 of the person 4. The determination system 201 is schematically and exemplarily illustrated in more detail in FIG. 8.

Figure 8:
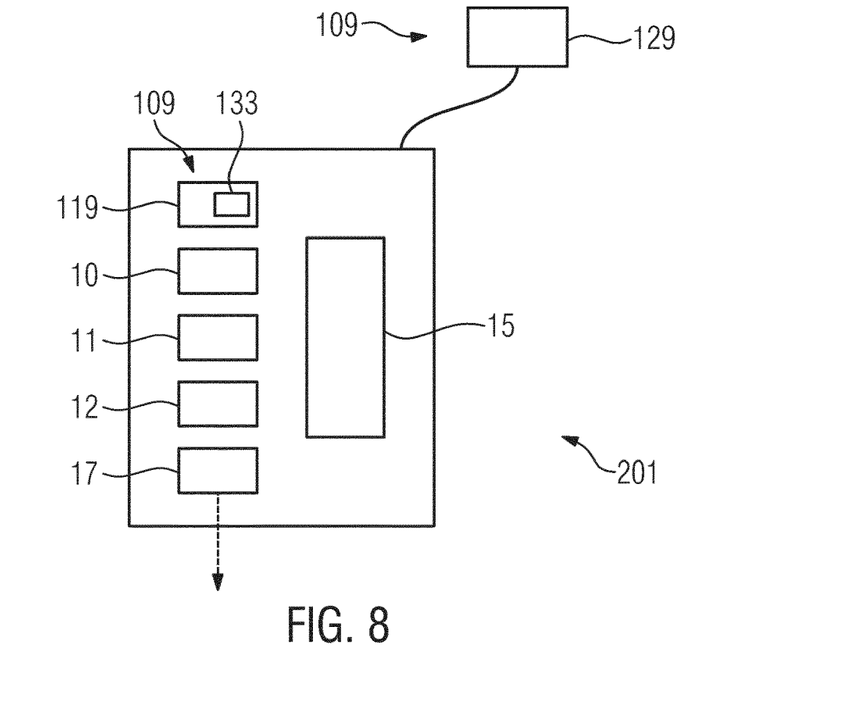
FIG. 8 shows schematically and exemplarily details of the further embodiment of the determination system for determining a HF risk.

The determination system 201 comprises a feet cardiogram measuring unit 119 for measuring the cardiogram via the feet 230 of the person 4, while the person 4 stands on the feet cardiogram measuring unit 119. As schematically and exemplarily illustrated in FIG. 9, the determination system 201 may comprise two pairs 140, 141 of sensors, which are preferentially flat, wherein per foot one sensor can be used for measuring the current and the other sensor may be used for measuring the voltage, in order to measure the impedance cardiogram. Each foot of the person 4 stands on a respective pair of flat sensors 140, 141, i.e. of electrodes. The feet cardiogram measuring unit 119 also comprises a load cell for measuring the weight of the person 4. Moreover, the feet cardiogram measuring unit 119 can be adapted to determine the body composition of the person 4. The determination system 201 can therefore also be regarded as being a scale with an integrated HF risk determination functionality, wherein the scale can also be adapted to determine the body composition of the person 4. As an alternative to measuring the impedance cardiogram or in addition to measuring the impedance cardiogram, the determination system can be adapted to measure a ballistocardiogram. For measuring the ballistocardiogram the load cell 133 might be used, which is also used for measuring the weight of the person 4. However, it is also possible to use another device integrated into the determination system 201 for measuring the ballistocardiogram like another load cell or an accelerometer. For detecting potentiation the person might do a few exercises, in order to increase the frequency, and step on the determination system 201 before theses exercises and after these exercises, wherein the cardiogram measured before these exercises and measured after these exercises might be used for determining the HF risk. For instance, if due to the exercises the frequency of the left ventricular pressure has been increased, while the heights of the peaks of the left ventricular pressure have not increased, a disturbed FFR and hence a relatively high HF risk can be determined.

Similar to the determination system 1 described above with reference to FIG. 2, also the determination system 201 comprises a HF risk determination unit 10, a breathing rate providing unit 11, an alarm unit 12, a sending unit 17 and a controller 15. The sending unit 17 is adapted to send the determined HF risk to an external device 29. The breathing rate providing unit 11 can be adapted to determine the breathing rate based on the cardiogram measured via the feet by using known techniques like the technique disclosed in the article "Heart and respiratory rate detection on a bathroom scale based on the ballistocardiogram and the continuous wavelet transform" by S. Gilaberte et al., Conference Proceedings IEEE Engineering in Medicine and Biology, pages 2557 to 2260 (2010), which is herewith incorporated by reference.

Figure 9:
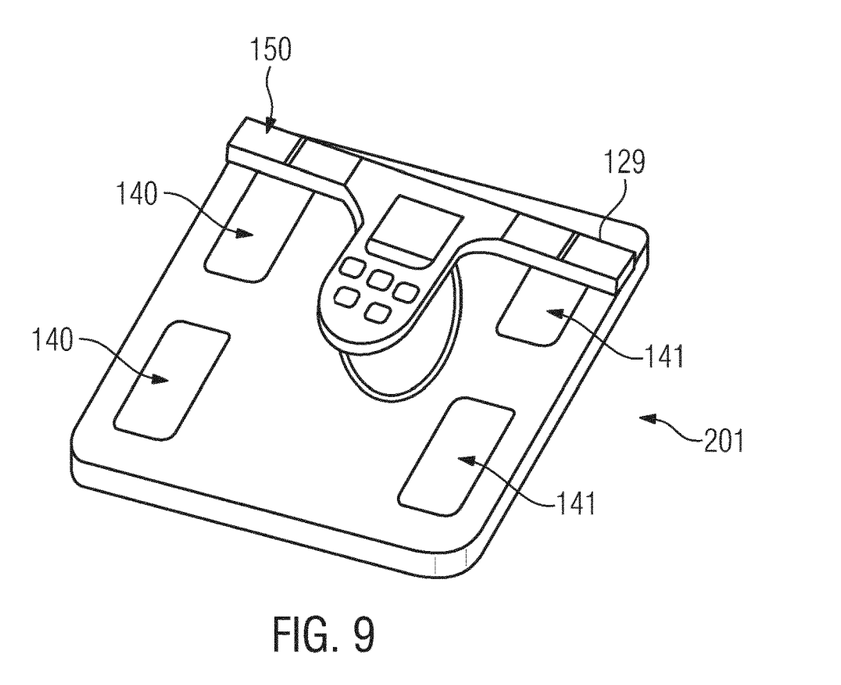
FIG. 9 shows schematically and exemplarily a top view on the further embodiment of the determination system for determining a HF risk.

The determination system 201 further comprises a handheld cardiogram measuring unit 129 for allowing for a measurement of the cardiogram via the handheld cardiogram measuring unit 129. Thus, for cases in which the electrodes 140, 141 at the feet 230 do not work, because, for instance, the user is wearing shoes, a handle 129 may be taken from the scale, i.e. from the determination system 201, to perform, for instance, an impedance cardiogram measurement. For this purpose also the handheld cardiogram measuring unit 129 can comprise corresponding sensing elements, i.e. electrodes 150. The handheld cardiogram measuring unit 129 and the feet cardiogram measuring unit 119 can be regarded as being components of a cardiogram providing unit 109.

The external device 29 can be, for instance, a patient data server within a hospital, a wrist watch, a smartphone, et cetera, wherein a health record of the person can be stored and updated by using the determined HF risk. Also the external device can be adapted to output an alarm if, for instance, the determined HF risk is provided as a value indicating the strength of the HF risk and if this value exceeds a predefined threshold.

The determination system can also be adapted to measure the cardiogram, in particular a ballistocardiogram, in a bed during the night such that the HF risk, especially the potentiation or the absence of it, can be determined while the person sleeps. For instance, a load cell can be integrated in a mattress of the bed for measuring a ballistocardiogram, while the person is in the bed. It is also possible that, for instance, an accelerometer is attached to the person for measuring the ballistocardiogram.

The accelerometer of the cardiogram providing unit 9 can also be used for determining whether movements of the person 4 are present, which could disturb the determination of the HF risk. For instance, an accelerometer signal generated by the accelerometer can be processed for determining whether it indicates movements which are not caused by a cardiac movement and which can disturb the HF risk determination. Rules can be provided defining whether a movement is not caused by a cardiac movement and can disturb the HF risk determination based on the accelerometer signal. For instance, frequencies and/or amplitudes of the accelerometer signal can be used for this determination. If such a movement has been detected, the corresponding part of the cardiogram might not be used for the HF risk determination. Alternatively, the corresponding part might be corrected for motion artifacts by using known motion artifact correction techniques. For instance, the technique disclosed in the article "Reduction of periodic motion artifacts in photoplethysmograhpy" by R. Wijshoff et al., IEEE Transactions on Biomedical Engineering (2016), which is herewith incorporated by reference, might be used for correcting this part of the cardiogram, before determining the HF risk. Instead of the accelerometer of the cardiogram providing unit another device for determining the movement of the person can be used. For instance, another accelerometer attached to the chest or to another part of the person can be used for providing a signal to be used for detecting a movement which is not caused by a cardiac movement and which can disturb the HF risk determination.

Although in an above described embodiment the breathing rate is determined based on the provided cardiogram, in other embodiments an extra breathing rate sensor can be used for providing the breathing rate. For instance, a chest belt or a flow sensor may be used for determining the breathing rate. The breathing rate can be used to detect shortness of breath and it can be detected whether this shortness of breath is correlated with physical activity measured by the accelerometer, in order to determine the HF risk.

The HF risk determination unit is preferentially adapted to determine the HF risk without using baselines, i.e. data of the person measured, for instance, at the beginning of the monitoring process. Preferentially, the HF risk determination unit is adapted to determine the HF risk based on a currently measured cardiogram. In this regard the HF risk determination unit can be regarded as being a local, in time, detection system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Procedures like the determination of the breathing rate based on the cardiogram, the determination of the HF risk, et cetera performed by one or several units or devices can be performed by any other number of units or devices. These procedures and/or the control of the determination system for determining a HF risk for a subject in accordance with the determination method for determining a HF risk for a subject can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a determination system for determining a heart failure risk for a subject. The determination system is adapted to provide a cardiogram selected from a group consisting of a ballistocardiogram, a seismocardiogram and an impedance cardiogram of the subject, to detect at least one of a presence of a PESP and a disturbed force-frequency relation based on the provided cardiogram and to determine the heart failure risk based on this detection. By using the detection of the presence of the PESP and/or of a disturbed force-frequency relation, the heart failure risk can be reliably determined. In particular, it can be determined that the heart failure risk is relatively large, if a PESP is not present and/or if the force-frequency relation is disturbed.

The invention claimed is:

1. A determination system for determining a heart failure risk for a subject, wherein the determination system comprises:
    a controller configured to:
        receive a cardiogram selected from a group consisting of a ballistocardiogram, a seismocardiogram and an impedance cardiogram of the subject, wherein the cardiogram is measured noninvasively; and
        determine the heart failure risk based on the cardiogram,
    wherein the controller is configured to:
        determine peak values for different times, which are indicative of heights of the peaks of the left ventricular pressure over time, based on the provided cardiogram for determining a temporal behavior of characteristics of the left ventricular pressure,
        provide rules which include a first peak value threshold and a second peak value threshold, different than the first peak value threshold, and which define the detection of the presence of a postextrasystolic potentiation (PESP) depending on whether a) a peak value is smaller than the first peak value threshold and b) the following peak value is not larger than the second peak value threshold, and
        determine the heart failure risk based on the determined temporal behavior and the provided rules.

2. The determination system as defined in claim 1, wherein the controller is further adapted to detect a presence of a disturbed force-frequency relation (FFR) based on the provided cardiogram and to determine the heart failure risk also based on the detection of the presence of the disturbed force-frequency relation.

3. The determination system as defined in claim 2, wherein the controller is adapted to:
    determine further, for determining the temporal behavior of characteristics of the left ventricular pressure, frequency values for different times, which are indicative of the frequency of the left ventricular pressure over time, based on the provided cardiogram,
    provide rules defining the heart failure risk depending on the determined temporal behavior, wherein the rules define a detection of the disturbed force-frequency relation based on the determined temporal behavior, and
    determine the heart failure risk based on the determined temporal behavior and the provided rules.

4. The determination system as defined in claim 3, wherein the controller is adapted to provide rules which define the detection of the disturbed force frequency relation depending on whether the frequency values increase over time, while the peak values do not increase over time.

5. The determination system as defined in claim 1, wherein the determination system further comprises an activity state providing unit for providing an indication of the activity state of the subject, wherein the controller is adapted to determine the heart failure risk also under consideration of the activity state, wherein controller is adapted to provide rules including an activity frequency threshold that depends on the activity state and which define the heart failure risk also depending on whether the frequency values are larger than the activity frequency threshold for the respective activity state.

6. The determination system as defined in claim 1, wherein the controller is adapted to determine frequency values for different times, which are indicative of the frequency of the left ventricular pressure over time, based on the cardiogram for further determining the temporal behavior, and to provide rules which include a frequency deviation threshold and which define the heart failure risk also depending on whether a deviation between temporally consecutive frequency values is larger than a frequency deviation threshold.

7. The determination system as defined in claim 1, wherein the determination system comprises a unit for providing a breathing rate of the subject, wherein the controller is adapted to determine the heart failure risk also based on the provided breathing rate.

8. The determination system as defined in claim 7, wherein the unit for providing the breathing rate of the subject is adapted to determine the breathing rate based on the cardiogram and to provide the determined breathing rate.

9. The determination system as defined in claim 1, further comprising a unit for measuring the cardiogram via feet of the subject, while the subject stands on the unit.

10. The determination system as defined in claim 9, wherein the unit is further adapted to measure the weight of the subject, wherein the unit comprises a load cell for measuring the weight and the cardiogram.

11. The determination system as defined in claim 9, further comprising a handheld unit for allowing for a measurement of the cardiogram via the handheld unit.

12. A method for determining a heart failure risk for a subject, wherein the method comprises:
providing a cardiogram selected from a group consisting of a ballistocardiogram, a seismocardiogram and an impedance cardiogram of the subject, wherein the cardiogram is measured noninvasively;
determining the heart failure risk based on the cardiogram by a controller, wherein the controller:
  i) determines peak values for different times, which are indicative of heights of the peaks of the left ventricular pressure over time, based on the provided cardiogram for determining a temporal behavior of characteristics of the left ventricular pressure,
  ii) provides rules which include a first peak value threshold and a second peak value threshold, different than the first peak value threshold, and which define the detection of the presence of a postextrasystolic potentiation depending on whether a) a peak value is smaller than the first peak value threshold and b) the following peak value is not larger than the second peak value threshold, and
  iii) determines the heart failure risk based on the determined temporal behavior and the provided rules.

13. A non-transitory computer program for determining a heart failure risk for a subject, the computer program comprising program code means for causing a determination system to carry out a determination method, when the computer program is run on the determination system, the method comprising:
providing a cardiogram selected from a group consisting of a ballistocardiogram, a seismocardiogram and an impedance cardiogram of the subject, wherein the cardiogram is measured noninvasively;
determining the heart failure risk based on the cardiogram by a controller, wherein the controller:
  i) determines peak values for different times, which are indicative of heights of the peaks of the left ventricular pressure over time, based on the provided cardiogram for determining a temporal behavior of characteristics of the left ventricular pressure,
  ii) provides rules which include a first peak value threshold and a second peak value threshold, different than the first peak value threshold, and which define the detection of the presence of a postextrasystolic potentiation depending on whether a) a peak value is smaller than the first peak value threshold and b) the following peak value is not larger than the second peak value threshold, and
  iii) determines the heart failure risk based on the determined temporal behavior and the provided rules.

* * * * *